United States Patent
Singh et al.

(10) Patent No.: US 9,861,534 B2
(45) Date of Patent: *Jan. 9, 2018

(54) SYSTEM AND METHOD FOR MANUFACTURING USING A VIRTUAL FRAME OF REFERENCE

(75) Inventors: Rajesh Kumar Singh, Cincinnati, OH (US); Jeremy Georges Bertin, Plainfield (CA); Thomas Keith Olschner, West Chester, OH (US); Jon Richard Rossiter, Liberty Township, OH (US); Steven Arthur Marshall, Stirling (CA)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/480,039

(22) Filed: May 24, 2012

(65) Prior Publication Data

US 2013/0317636 A1 Nov. 28, 2013

(51) Int. Cl.
*A61F 13/00* (2006.01)
*A61F 13/15* (2006.01)

(52) U.S. Cl.
CPC .............................. *A61F 13/15772* (2013.01)

(58) Field of Classification Search
None
See application file for complete search history.

(56) References Cited

U.S. PATENT DOCUMENTS

| | | |
|---|---|---|
| 4,007,866 A | 2/1977 | Traise |
| 4,680,205 A | 7/1987 | Lerner et al. |
| 4,837,715 A | 6/1989 | Ungpiyakul et al. |
| 4,926,048 A | 5/1990 | Lerner et al. |
| 4,945,252 A | 7/1990 | Lerner et al. |
| 5,018,213 A | 5/1991 | Sikes |
| 5,045,135 A * | 9/1991 | Meissner et al. ............... 156/64 |
| 5,239,547 A | 8/1993 | Tomiyama et al. |
| 5,256,883 A | 10/1993 | Weichmann et al. |
| 5,359,525 A * | 10/1994 | Weyenberg ................... 700/124 |
| 5,659,538 A | 8/1997 | Stuebe et al. |
| 5,732,529 A | 3/1998 | Dey et al. |
| 5,766,389 A | 6/1998 | Brandon et al. |
| 5,873,392 A | 2/1999 | Meyer et al. |
| 5,930,139 A | 7/1999 | Chapdelaine et al. |
| 5,932,039 A | 8/1999 | Popp et al. |
| 5,964,970 A | 10/1999 | Woolwine et al. |
| 5,980,087 A | 11/1999 | Brandon et al. |
| 6,026,172 A | 2/2000 | Lewis, Jr. et al. |
| 6,033,502 A | 3/2000 | Coenen et al. |
| 6,059,710 A | 5/2000 | Rajala et al. |
| 6,074,333 A | 6/2000 | Rajala et al. |
| 6,092,002 A | 7/2000 | Kastman et al. |
| 6,097,427 A | 8/2000 | Dey et al. |
| 6,165,306 A | 12/2000 | Rajala |
| 6,245,168 B1 | 6/2001 | Coenen et al. |
| 6,253,159 B1 | 6/2001 | Bett et al. |

(Continued)

*Primary Examiner* — Christopher E Everett

(74) *Attorney, Agent, or Firm* — George H. Leal; Megan Chorey Hymore

(57) ABSTRACT

System and method to use a virtual frame of reference to evaluate and control a manufacturing system. Electronic images from a vision system may be analyzed using the virtual frame of reference to control the phasing of devices in the manufacturing system and to generate alerts.

8 Claims, 8 Drawing Sheets

(56) References Cited

U.S. PATENT DOCUMENTS

| | | | | |
|---|---|---|---|---|
| 6,266,436 | B1 | 7/2001 | Bett et al. | |
| 6,352,497 | B1 | 3/2002 | Hensley et al. | |
| 6,354,984 | B1 | 3/2002 | Hensley et al. | |
| 6,404,910 | B1 * | 6/2002 | Ungpiyakul et al. | 382/141 |
| 6,408,917 | B1 | 6/2002 | Bett et al. | |
| 6,444,064 | B1 | 9/2002 | Henry et al. | |
| 6,520,236 | B1 | 2/2003 | Rajala | |
| 6,527,902 | B1 | 3/2003 | Rajala | |
| 6,553,270 | B1 | 4/2003 | Houle et al. | |
| 6,565,686 | B2 | 5/2003 | Bett et al. | |
| 6,703,846 | B2 | 3/2004 | Delzer et al. | |
| 6,743,314 | B2 | 6/2004 | Henry et al. | |
| 6,764,563 | B2 | 7/2004 | Henry et al. | |
| 6,801,828 | B2 | 10/2004 | Popp et al. | |
| 6,820,022 | B2 | 11/2004 | Popp et al. | |
| 6,829,516 | B2 | 12/2004 | Popp et al. | |
| 6,845,278 | B2 | 1/2005 | Popp et al. | |
| 6,904,330 | B2 * | 6/2005 | Popp et al. | 700/110 |
| 6,909,106 | B2 | 6/2005 | Ungpiyakul et al. | |
| 6,927,857 | B2 * | 8/2005 | Koele et al. | 356/431 |
| 6,955,733 | B2 | 10/2005 | Miller et al. | |
| 7,039,632 | B2 | 5/2006 | McCormick | |
| 7,047,852 | B2 | 5/2006 | Franklin et al. | |
| 7,082,347 | B2 | 7/2006 | Popp et al. | |
| 7,092,777 | B2 * | 8/2006 | Reade et al. | 700/103 |
| 7,123,981 | B2 * | 10/2006 | Dollevoet et al. | 700/143 |
| 7,130,709 | B2 * | 10/2006 | Popp et al. | 700/122 |
| 7,130,710 | B2 * | 10/2006 | Popp et al. | 700/125 |
| 7,155,746 | B2 | 1/2007 | Schorr et al. | |
| 7,162,319 | B2 | 1/2007 | Popp et al. | |
| 7,171,283 | B2 * | 1/2007 | Popp et al. | 700/121 |
| 2001/0038709 | A1 * | 11/2001 | Bett et al. | 382/141 |
| 2001/0048760 | A1 * | 12/2001 | Bett et al. | 382/141 |
| 2002/0139484 | A1 | 10/2002 | Henry et al. | |
| 2003/0136495 | A1 | 7/2003 | Miller et al. | |
| 2004/0028268 | A1 * | 2/2004 | Popp et al. | 382/141 |
| 2005/0154485 | A1 * | 7/2005 | Popp et al. | 700/124 |
| 2007/0071324 | A1 * | 3/2007 | Thakur | 382/199 |
| 2009/0195791 | A1 * | 8/2009 | Lucia et al. | 356/614 |

* cited by examiner

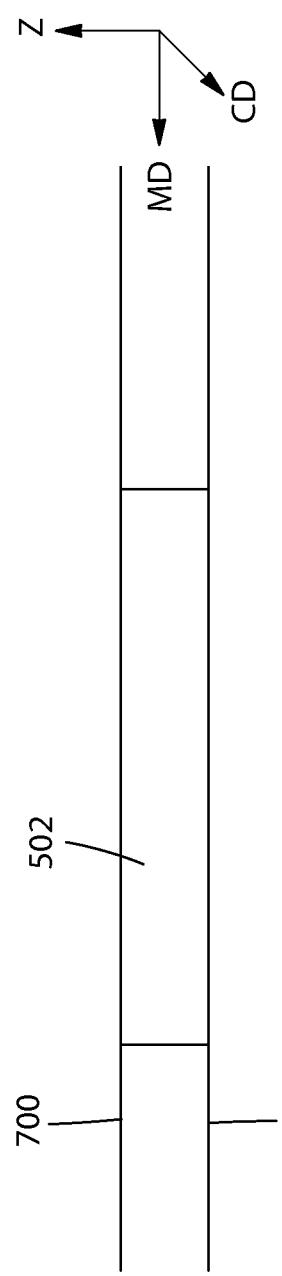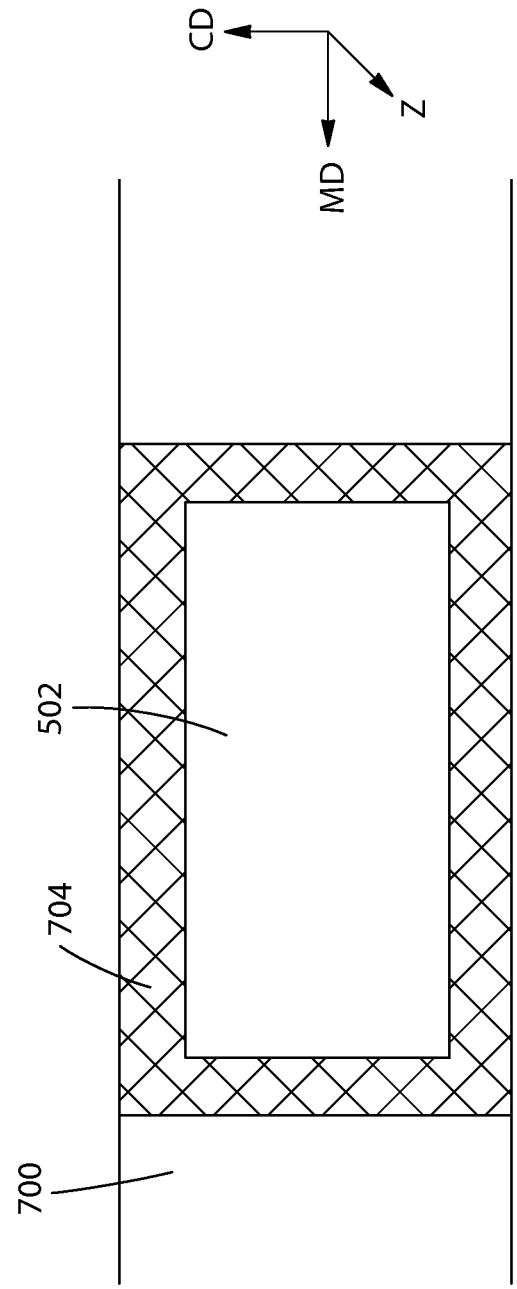

SYSTEM AND METHOD FOR MANUFACTURING USING A VIRTUAL FRAME OF REFERENCE

CROSS REFERENCE TO RELATED APPLICATION

This application claims the benefit of International Application No. PCT/US11/37938 filed on May 25, 2011, designating the U.S.

FIELD OF THE INVENTION

The present invention relates generally to a system and method for manufacturing, and more particularly to a system and method using a virtual frame of reference to electronically evaluate the position of components used in the manufacturing process.

BACKGROUND OF THE INVENTION

During the manufacturing of consumer goods, the position of components used in the manufacturing process may affect the overall quality of the goods and the acceptance of the goods by consumers. Consumers often desire consistency in the configuration of purchased goods for both functional and aesthetic reasons. To ensure consistency throughout the manufacturing process, components must be positioned uniformly.

By way of example, many disposable absorbent products such as diapers and feminine hygiene products include a core of absorbent material positioned between a top sheet and a bottom sheet. Variations in the placement of the core within the finished good can result in leakage and reduce the functionality of the product. Even if the placement of the core and other components do not affect the functionality of the product, consumers expect each product to maintain the same look and feel as one another. For example, a winged pantiliner having an off-center or skewed core may create confusion for a consumer as to the best way to place such a pantiliner in her undergarment. Or, for example, the placement of a popular design on a diaper (e.g., a popular children's character, a team logo, and other familiar designs) must be consistently placed, in order to ensure that the design is fully shown (e.g., that a headless character is not shown, a team logo is not missing the name of the team's city, and other inconsistencies).

Based on the foregoing, developing new vision systems that automate a manufacturing process to produce consumer goods can be challenging and difficult.

SUMMARY OF THE PRESENT INVENTION

A controller for a manufacturing system is shown and described herein. The controller includes one or more processors and one or more memory devices communicatively coupled to the one or more processors. The one or more memory devices store machine instructions that, when executed by the one or more processors, cause the one or more processors to receive an electronic image of a component used in the manufacturing system. The instructions also cause the one or more processors to analyze the electronic image using a virtual frame of reference to determine a location value associated with the component, to compare the location value and a setpoint, and to generate a phasing command for a machine in the manufacturing system based on the comparison.

A computerized method for determining and controlling the positions of components in a manufacturing system is shown and described herein. The method includes capturing an electronic image of a component used in the manufacturing system and analyzing, by one or more processors, the electronic image using a virtual frame of reference to determine a location value associated with the component. The method further includes comparing the location value and a setpoint and also includes generating a phasing command for a machine in the manufacturing system based on the comparison.

A computerized method for controlling a component transformation in a manufacturing system is shown and described herein. The method includes receiving, at one or more processors, electronic images of components used by the manufacturing system to produce a manufactured good and classifying the images into two or more subpopulations. The method also includes analyzing the images, by the one or more processors, using a virtual frame of reference to determine location values associated with the components. The method further includes using the location values to determine a mathematical characteristic of each of the subpopulations and using the mathematical characteristic to generate a phasing command for a machine in the manufacturing system.

BRIEF DESCRIPTION OF THE DRAWINGS

The following detailed description of the present disclosure can be best understood when read in conjunction with the following drawings, where like structure is indicated with like reference numerals and in which:

FIG. 7A is a side-view illustration of an individual core located between a top sheet and a back sheet;
and
FIG. 7B is a top-view illustration of an individual core located between a crimped topsheet and back sheet.

Figure 1:
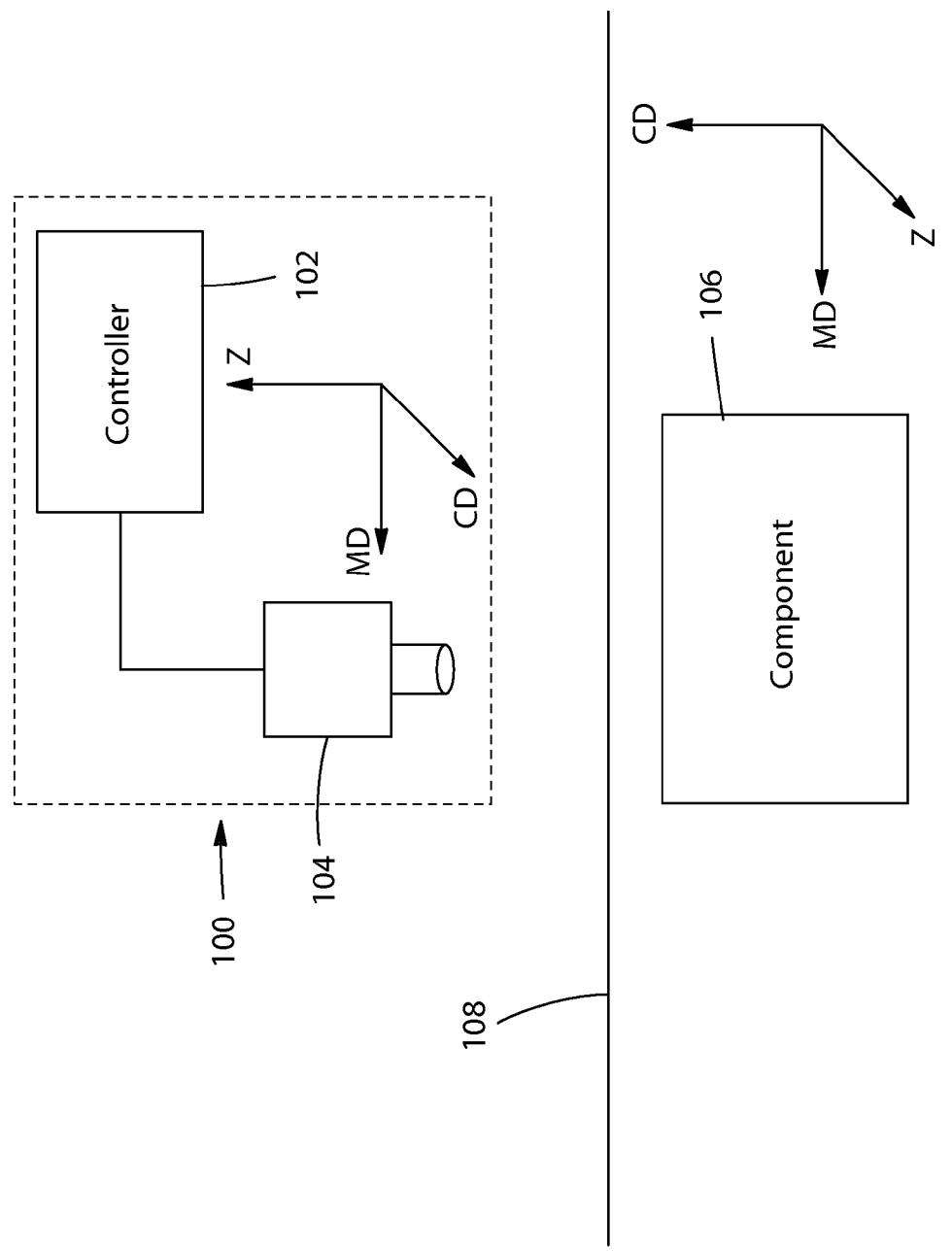
FIG. 1 is a schematic illustration of a vision system.

Individual aspects of the drawings will be more fully apparent and understood in view of the detailed description that follows.

DETAILED DESCRIPTION

Present techniques to help automate the manufacture of goods often require using additional sensors, providing timing marks on the product itself, and/or making manual adjustments to the manufacturing process. It has been discovered that utilizing a virtual frame of reference allows for a reduction in the number of devices used by the manufacturing process and improves the overall quality of the manufactured goods. In addition, utilizing virtual frames of reference helps to automate the manufacturing process, thereby reducing the possibility of human error in adjusting the process.

DEFINITIONS

As used herein, the following terms are defined as follows:

"Disposable absorbent article" refers to feminine hygiene products (e.g., pantiliners or pads), disposable diapers, pull-ons, training pants, and adult incontinence articles.

"Machine direction" (MD) refers to the direction of movement of a component along a manufacturing line.

"Cross direction" (CD) refers to the direction substantially perpendicular or perpendicular to the MD and across the component as it moves along a manufacturing line.

"Component" refers to any material, part, or combination of materials and/or parts used in the construction of a final good by a manufacturing system.

"Phase" refers to the positional relationship between two or more parts of a machine that performs repetitive motion. For example, phase may refer to the relative position of a roller that unwinds a roll of material used in the manufacturing process. In another example, phase may also refer to the relative position of a punch that stamps apertures into a component used in the manufacturing process. When utilized as verbs, the terms "phasing," "phased," "phase," and the like refer to the act of changing the phase of a device from one phase to another. For example, the act of phasing a roller may refer to advancing or retarding the rotation of the roller about its primary axis.

"Component transformation" refers to any action performed by the manufacturing process on one or more components used to produce the final consumer goods. In general, a component transformation may be any change to the configuration of a component performed by the manufacturing process. Some component transformations may only change the spatial properties of a component, while others may change the physical properties of the component. For example, rotating, flipping, and reorienting components are component transformations. Increasing or retarding the speed of motion of a component within the manufacturing process may also be component transformations. Other examples of transformations include cutting components, joining components, separating components from one another, changing the shapes of components, perforating components, punching or cutting apertures into components, and changing the look of components (e.g., by applying graphics, paint, dyes, or the like).

"Controller" refers to any electronic device or system that provides control commands to another electronic and/or mechanical system. A controller includes one or more processors (e.g., a microprocessor, central processing unit, application-specific integrated circuit, or the like). A controller may also include one or more memory devices (e.g., a RAM, ROM, non-volatile memory, flash memory, non-transitory memory, hard drive, disk drive, or any other electronic device capable of storing machine instructions) that communicate locally or remotely with the one or more processors. The one or more memory devices store machine instructions that, when executed by the one or more processors, cause the one or more processors to provide the control commands. Non-limiting examples of controllers include personal computers, servers, programmable logic controllers (PLCs), tablet computers, handheld computing devices, mobile telephones, distributed computing systems, cameras, and electronic displays.

Vision Systems Using Virtual Frames of Reference

In general, a vision system includes one or more cameras that capture images of components as they move through the manufacturing process. Any known type of electronic camera may be used. For example, a camera may be a charge-coupled device, a CMOS-pixel based device, or the like. The image data captured by a camera is provided to one or more controllers for further analysis. A camera may have one or more controllers integrated as part of the device (e.g., within the same housing as the camera) and/or transmit the image data to one or more controllers external to the camera. The one or more controllers analyze the image data using a virtual frame of reference to determine if the manufacturing process needs to be adjusted. If an adjustment is needed, the one or more controllers generate control commands that change how one or more upstream and/or downstream component transformations are performed.

Referring now to FIG. 1, an illustrative schematic of vision system 100 is shown. Vision system 100 includes camera 104. As shown, camera 104 may be positioned in a fixed location and capture an electronic image of a component 106, as it passes vision system 100 in the machine direction along manufacturing line 108. Camera 104 may be oriented in any number of positions in relation to the direction of motion of component 106. For example, camera 104 may be positioned above or below component 106, along the side of component 106, or somewhere therebetween. Camera 104 may take continuous images (e.g., video) or still-frames that are captured periodically or in response to receiving a trigger from an upstream and/or downstream device.

Camera 104 provides a captured electronic image to controller 102, which analyzes the image using a virtual frame of reference to determine if an adjustment to the manufacturing process is needed. The virtual frame of reference allows analysis of the spatio- or spatio-temporal location of component 106 as it relates to the manufacturing process and/or other components within the manufacturing process. Controller 102 may analyze the position, orientation, and/or timing of component 106 as it passes vision system 100 to determine if an upstream or downstream component transformation requires adjustment. For example, if an upstream component transformation reorients component 106, controller 102 may analyze the position of component 106 relative to a setpoint position and send a control signal to the upstream process to ensure that the position of future components approaches the setpoint position. In another example, controller 102 may analyze the timing of component 106 (e.g., to determine if component 106 reaches vision system 100 earlier or later than expected) and advance or retard an upstream or downstream transformation device, in order to ensure that the component 106 reaches the vision system 100 at the expected time.

In general, a virtual frame of reference allows the location of a component to be determined relative to one or more coordinates (e.g., points, lines, areas, or the like) in the image. If the one or more cameras of a vision system remain at fixed locations, each image may be viewed as a set of coordinates, allowing the location of the component within an image to be determined. For example, the number of pixels from an edge of the image to an edge of the component within the image can be used to determine the position of the component. Similarly, the timing of when images are captured allows for comparisons to be made between multiple components that pass the vision system. In some cases, images may be captured continuously, periodically, and/or in response to an upstream or downstream trigger. When the camera remains in a fixed position, a virtual frame of reference may be used to analyze a component's location within an image and to adjust the manufacturing process. If the camera is not in a fixed position (e.g., moving), a virtual frame of reference may still be used, but must be adjusted to compensate for the movement of the camera. It is to be understood that while the descriptions herein primarily refer to camera positions that allow the edges of images to correspond to the MD and CD axes, this is merely illustrative and a vision system's camera may be oriented in any position to create a virtual frame of reference.

Using the virtual frame of reference, a vision system may make any number of determinations relating to the position and/or timing of a component passing the vision system. For example, a controller may determine the MD length, corner locations, skew, CD placement, and/or MD placement of a component. Additionally, a controller may determine the location of any distinguishing features on the component (e.g., an aperture, visual indicia, a physical characteristic, or the like). For example, a controller may determine the CD and/or MD placement of apertures on a component.

The controller utilizes the determined positions of a component relative to the virtual frame of reference to adjust the manufacturing process. The controller may compare data relating to the actual position of the component to one or more setpoints, to determine if the manufacturing process needs to be adjusted. In some cases, the setpoints may be generated by the controller by analyzing one or more populations of components that pass the vision system. For example, an average position for a population of prior components may be used to generate a setpoint to analyze future components passing the vision system. In other cases, some or all of the setpoints may be preloaded into the controller.

Figure 2:
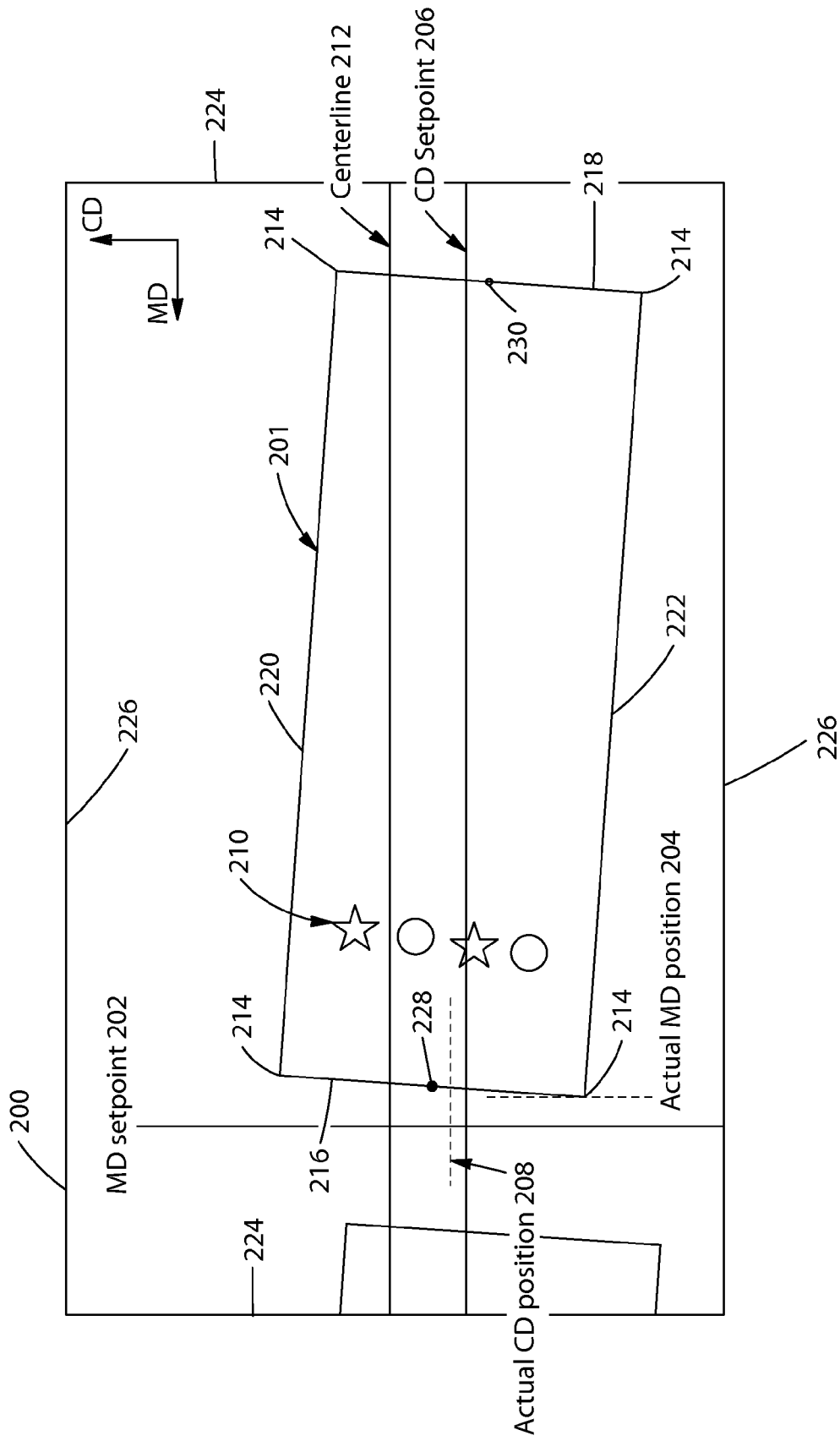
FIG. 2 is an illustration of an electronic image.

Referring now to FIG. 2, an illustration of an electronic image 200 is shown. Image 200 is captured as component 201 passes the camera of a vision system and analyzed to determine the location of component 201 relative to a virtual frame of reference. For example, this analysis may include determining the leading and trailing edges of component 201 in the machine direction (e.g., edges 216 and 218, respectively), locating one or more corners 214 of component 201, and/or determining the location of one or more edges of component 201 in the cross-direction (e.g., edges 220 and 222). In cases where component 201 is of a substantially quadrilateral shape, the controller may locate the corners using the intersection of the edges of component 201. In cases where component 201 is not of a quadrilateral shape, the controller may analyze the curvature of the leading and trailing edges of component 201 in the machine direction to approximate the location of the corners. In addition to determining the spatial characteristics of component 201 within image 200, a controller may also determine the location of distinguishing features 210 (e.g., apertures, visual indicia, or the like).

The location of component 201 may be defined relative to any fixed point within image 200. For example, actual MD position 204 may be located relative to leading or trailing edges 224 of image 200 in the machine direction (e.g., by counting the number of pixels between an edge 224 and actual MD position 204, or the like). In another example, the actual CD position 208 may be measured using the location of the corners 214 of component 201. Another exemplary measurement includes the CD position of features 210, which may be determined relative to a virtual location in the cross-direction (e.g., centerline 212 of the image 200, or the like). Similarly, the MD position of features 210 may be determined relative to the leading edge 216 of component 201, or any other location in the machine direction.

In general, MD-related measurements within the virtual frame of reference also rely on a temporal component, since MD positions are dependent on the timing of the manufacturing system. In other words, image 200 must be captured at the proper moment, to ensure that positional measurements are meaningful. In some cases, the capturing of image 200 may be triggered periodically or triggered by the performance of a downstream transformation. In general CD-related measurements within the virtual frame of reference may be made with regard to the position of the camera. For example, CD-related measurements may be made with regard to the fixed location of a mirror plate or other physical location associated with the position of the camera.

Non-limiting examples of measurements that can be made by analyzing image 200 are as follows:

The MD length of component 201 ("Length$_{MD}$") may be determined as:

Length$_{MD}$=MD trailing edge−MD leading edge using the difference between MD edges 216 and 218. In other examples, the length of the component may be determined using the difference between any two points on the perimeter of the component.

The skew of component 201 may be determined using the locations of 214. For example, the skew may be determined by using the following equation:

$$\text{Skew} = (CD\ midpoint_{lead} - CD\ midpoint_{trail}) * \left( \frac{2 * length_{MD}}{MD\ \text{distance between midpoints}} \right)$$

where CD midpoint$_{lead}$ is the CD midpoint 228 of the corners 214 on the MD leading side 216 of component 201, CD midpoint$_{trail}$ is the CD midpoint 230 of the corners 214 on the MD trailing side 218 of component 201, length$_{MD}$ is the length of the component in the MD direction (as determined above), and MD distance is the MD distance between midpoints 228, 230.

The CD placement of component 201 may be determined using the locations of its corners 214. For example, the CD placement (Placement$_{CD}$) may be determined using the following equation:

$$Placement_{CD} = avg(CD\ \text{midpoints}) = \frac{CD\ midpoint_{trail} - CD\ midpoint_{lead}}{2}$$

where CD midpoint$_{lead}$ is the CD midpoint 228 of corners 214 on the MD leading side 216 of component 201 and CD midpoint$_{trail}$ is the CD midpoint 230 of the corners 214 on the MD trailing side 218 of component 201.

The MD placement of the component may be determined using the leading edge of the component in MD direction. For example, the MD placement of the component may be determined relative to an edge of the electronic image as follows:

Placement$_{MD}$=MD leading edge−Image$_{lead}$ where Image$_{lead}$ is the location of edge 224 of image 200 image in the leading machine direction and MD leading edge is the actual MD position 204.

The CD and/or MD placement of distinguishable features 210 of component 201 may also be determined. For example, the CD placement of features 210 (Feature Placement$_{CD}$) may be determined as follows:

Feature Placement$_{CD}$=CD edge of the 1st feature–
CD edge of the component

Similarly, the MD placement of the features (Feature Placement$_{MD}$) may be determined as follows:

Feature Placement$_{MD}$=MD edge of the 1st feature–
MD edge of the component

This way, the location of distinguishable features can also be located on component 201.

In some cases, a controller analyzing electronic image 200 may also maintain one or more setpoint locations indicative of where component 201 should be positioned. For example, a MD setpoint 202 may indicate where actual MD position 204 should be at the time electronic image 200 is taken. Similarly, a CD setpoint 206 may indicate the ideal location of actual CD position 208. The controller may use the setpoint locations to provide phasing commands and/or alerts to other upstream and/or downstream devices associated with the manufacturing process. For example, if the skew of the component is beyond an acceptable range of threshold values, an alert may be provided by the controller signifying that maintenance may be needed or a phasing command may be sent to a component transformation device. In another example, if actual MD position 204 is located on the trailing side of MD setpoint 202 along the MD axis, this may be indicative of component 201 reaching MD setpoint 202 earlier or later than expected. The controller may use this determination to advance or retard an upstream or downstream component transformation device, accordingly. Similarly, if controller 102 determines that any variation exists between CD setpoint 206 and actual CD position 208, controller 102 may send a phasing control command to an upstream or downstream component transformation device to adjust how components are positioned in the cross-direction.

A controller analyzing an image may perform any number of functions associated with the analysis of the image. In some cases, a controller may generate an alert and/or stop an operation of the manufacturing process, if the difference between a measurement and a setpoint is above a threshold. In other cases, the controller may issue one or more phasing commands that adjust the phasing of one or more transformations in the manufacturing process (e.g., issue one or more phasing commands to a component transformation device). Phasing commands may be either direct commands (e.g., if the controller provides direct control over the component transformation device) or indirect commands (e.g., indications of the determination provided to the controller that provides direct control over the component transformation device). In further cases, the controller may communicate with other computing devices, interface devices, and/or alarms, to receive and convey data about the image analysis.

Figure 3:
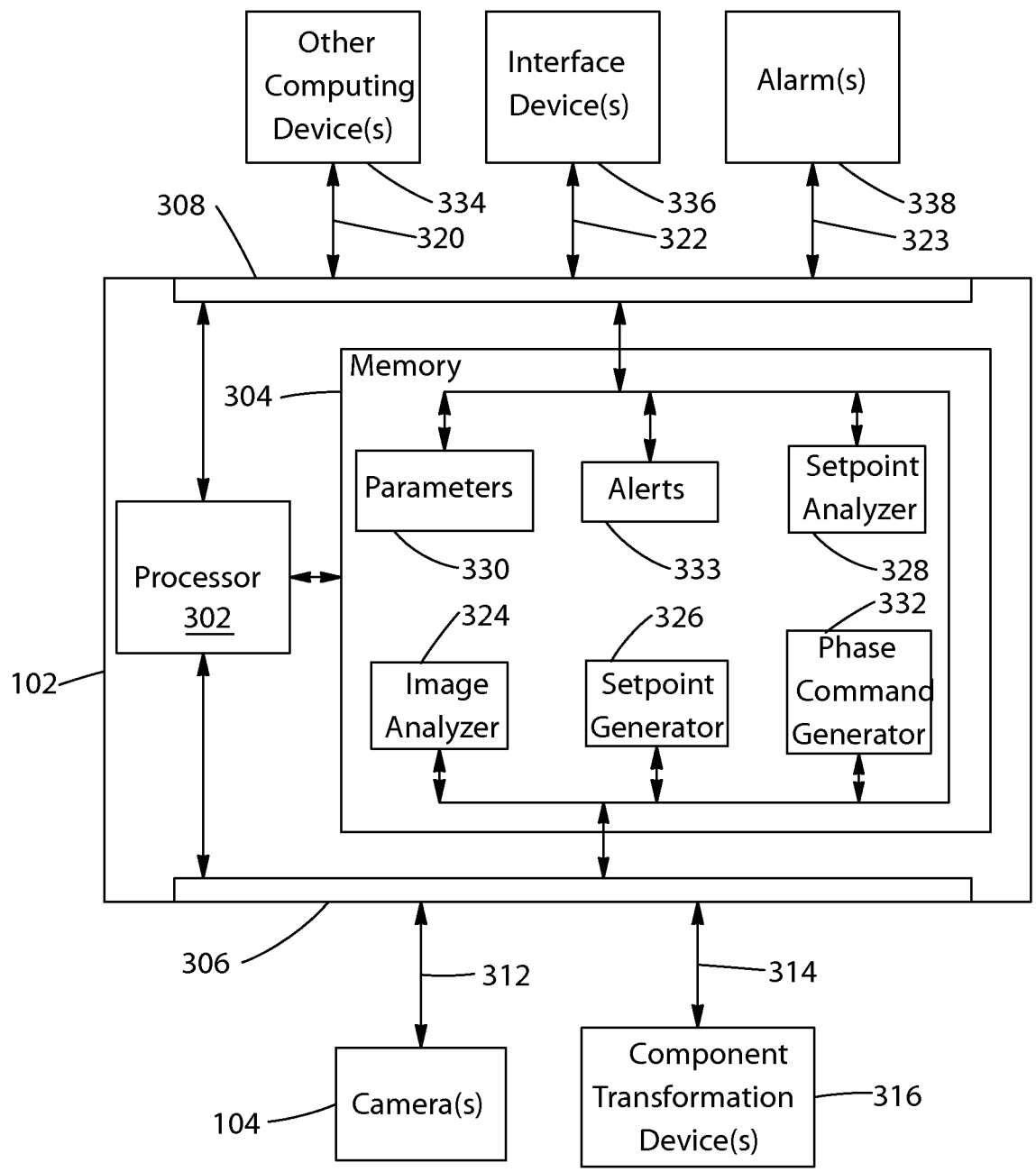
FIG. 3 is a schematic illustration of a controller.

Referring now to FIG. 3, a schematic illustration of controller 102 is shown. Controller 102 includes a processor 302, which may be one or more processors communicatively coupled to a memory 304, interface 306, and interface 308. Memory 304 may be any form of memory capable of storing machine-executable instructions that implement one or more of the functions disclosed herein, when executed by processor 302. For example, memory 304 may be a RAM, ROM, flash memory, hard drive, EEPROM, CD-ROM, DVD, other forms of non-transitory memory devices, or the like. In some cases, memory 304 may be any combination of different memory devices.

Controller 102 receives electronic images from one or more cameras 104 via connection 312 and interface 306. In some cases, controller 102 may also provide control over camera 104 via connection 312. For example, controller 102 may control when camera 104 captures an image using a timing value stored in parameters 330 and/or using a trigger received from another device (e.g., transformation devices 316, other computing devices 334, or the like). Controller 104 may also provide phasing commands to transformation devices 316 via interface 306 and connection 314. Transformation devices 316 may be any device that performs a component transformation in the manufacturing system. By way of non-limiting examples, transformation devices 316 may be punchers, cutters, crimpers, turners, embossers, winders, unwinders, lotion applicators, or the like.

Connections 312 and 314 may be any combination of hardwired or wireless connections. For example, connection 312 may be a hardwired connection to provide electronic images to controller 102, while connection 314 may be a wireless connection to provide phasing commands to transformation devices 316. In some cases, connections 312 and 314 may be part of a shared connection that conveys information between controller 102, camera 104, and transformation devices 316. In yet other cases, connections 312 and 314 may include one or more intermediary circuits (e.g., routers, modems, controllers, signal processors, and the like) and provide indirect connections to controller 102.

Interface 306 is configured to receive and transmit data between controller 102, camera 104, and/or other transformation devices 316. For example, interface 306 may include one or more wireless receivers if any of connections 312 or 314 are wireless. Interface 306 may also include one or more wired ports if any of connections 312 or 314 are wired connections.

Interface 308 may provide one or more wired or wireless connections between controller 102, other computing devices 334 (e.g., one or more controllers, computers, servers, portable devices, PLCs, or the like), interface devices 336 (e.g., one or more electronic displays, human-machine interfaces, speakers, or the like), and/or alarms 338 (e.g., one or more sirens, flashing lights, or the like) via connections 320, 322, and 323, respectively. For example, interface 308 may provide a wired connection between controller 102 and a display (e.g., an interface device 336) and a wireless connection between controller 102 and a remote server (e.g., other computing device 334) via the Internet.

Memory 304 is shown to include image analyzer 324, which is configured to receive and analyze the electronic images captured by camera 104. Image analyzer 324 detects the space occupied by a component within the image. In non-limiting examples, image analyzer 324 may detect a leading or trailing edge of a component in the machine direction, one or more edges in the cross-direction, and one or more corners of the component. In this way, image analyzer 324 may locate the perimeter of a component within the electronic image, and/or locate distinguishable features of the components (e.g., apertures, designs, protrusions, or the like).

Image analyzer 324 may also determine the location of a component in an image relative to another location and performs measurements based on the location. For example, the location of a point may be analyzed relative to another point in the image (e.g., a coordinate, an edge of the image, a fixed line, or the like). Non-limiting examples of measurements performed by image analyzer 324 include: MD length, skew, CD placement, MD placement, feature CD placement, and/or feature MD placement. Image analyzer 324 may also maintain an average of the measurements (e.g., a moving average, a weighted average, or the like) for a set number of components that are analyzed. For example, an average measurement may be maintained for the previous MD placement values for the last fifty components. In some cases, an average is only calculated using measurements for components when the manufacturing system is at full operational speed. Image analyzer 324 may also make one or more of the measurements based on a transformation yet to be performed on the component. For example, a downstream device in the manufacturing process (e.g., other computing device 334, component transformation device 316, or the like) may provide a trigger to controller 102, which causes camera 104 to capture an image in response. Such timing allows controller 102 to analyze the image with regard to the future transformations (e.g., in relation to a virtual cut line, placement of a feature onto the component, or the like).

Memory 304 is also shown to include a setpoint generator 326, which uses measurements from image analyzer 324 to generate one or more setpoints. In general, the setpoints may be coordinates, lines, or areas in the reference system that correspond to an expected measurement value associated with a component. In some cases, setpoint generator 326 may determine a setpoint using an average of measurements from image analyzer 324 for a set number of components. For example, setpoint generator 326 may calculate an MD setpoint using the average (e.g., a moving average, weighted average, or the like) of the MD leading edge of the last fifty components that have passed camera 104. Setpoint generator 326 may also utilize data from transformation devices 316 to determine a setpoint (e.g., a virtual cut line, where a feature is to be placed onto the component, or the like). In some cases, setpoint generator 326 may maintain a group of two or more setpoints for a measurement, if components passing camera 104 have different orientations. For example, if components periodically pass camera 104 in three different orientations, setpoint generator 326 may use the orientation of the latest component to select the appropriate setpoint.

Parameters 330 may include any number of user or system defined parameters that override or control the functions of controller 102. For example, parameters 330 may include parameters that specify how many components are analyzed by setpoint generator 326 before a setpoint is generated, a setpoint value that overrides a generated setpoint, when an alert is to be issued, or any other setting. Parameters 330 may be preloaded into memory 304 and/or specified via other computing devices 334 or interface devices 336. For example, a user utilizing a touchscreen display (e.g., an interface device 336) may change a setting in parameters 330.

Memory 304 may include a setpoint analyzer 328 that compares one or more measurements from image analyzer 324 to one or more setpoints. The one or more setpoints may be generated by setpoint generator 326 or preset in parameters 330. Setpoint analyzer 328 determines the difference between the measurement and the setpoint, in order to determine if further action needs to be taken by controller 102. Setpoint analyzer 328 may also compare the difference between the measurement and the setpoint to a threshold, in order to determine if further action is needed. In some cases, setpoint analyzer 328 may also utilize other variables (e.g., an offset, a multiplier, an average of measurements, or the like) as part of the determination.

If setpoint analyzer 328 determines that further action by controller 102 is needed, it may provide an indication of this determination to alerts 333. Alerts 333 may include, in non-limiting examples, messages indicating that a component should be rejected based on length, skew, CD placement, MD placement, aperture CD placement, aperture MD placement, or any other measurement from the electronic image. For example, if the skew of the component is outside of an acceptable range, controller 102 may generate an alert to a machine operator via interface devices 336 and/or alarms 338 that maintenance may be needed. In another example, alerts 333 may be provided to other computing devices 334 to keep track of the number of rejected components.

If setpoint analyzer 328 determines that further action by controller 102 is needed, it may also provide an indication of this determination to phase command generator 332. Phase command generator 332 generates phasing commands for transformation devices 316, which perform component transformations in the manufacturing system. In general, phase commands may cause the advancing or retarding of the processing of components by one or more component transformation devices 316. In some cases, a phase command may provide direct control over a component transformation device 316. In other cases, a phase command may be a command to other computing devices 334 (e.g., a controller) that causes the phasing of a component transformation device 316 (e.g., a crimper or turner). For example, a phase command may control when a crimper applies crimping to a component.

As can be appreciated, the vision systems described herein can be used to adjust any number of component transformations in manufacturing systems that produce any number of different types of goods. Such vision systems are able to automatically adjust a manufacturing system without user interaction and improve the overall quality of the finalized products. Any number of different types of manufacturing systems may be built by varying the number and type of transformation devices, and by utilizing one or more of the vision systems described herein to automate the system.

Figure 4:
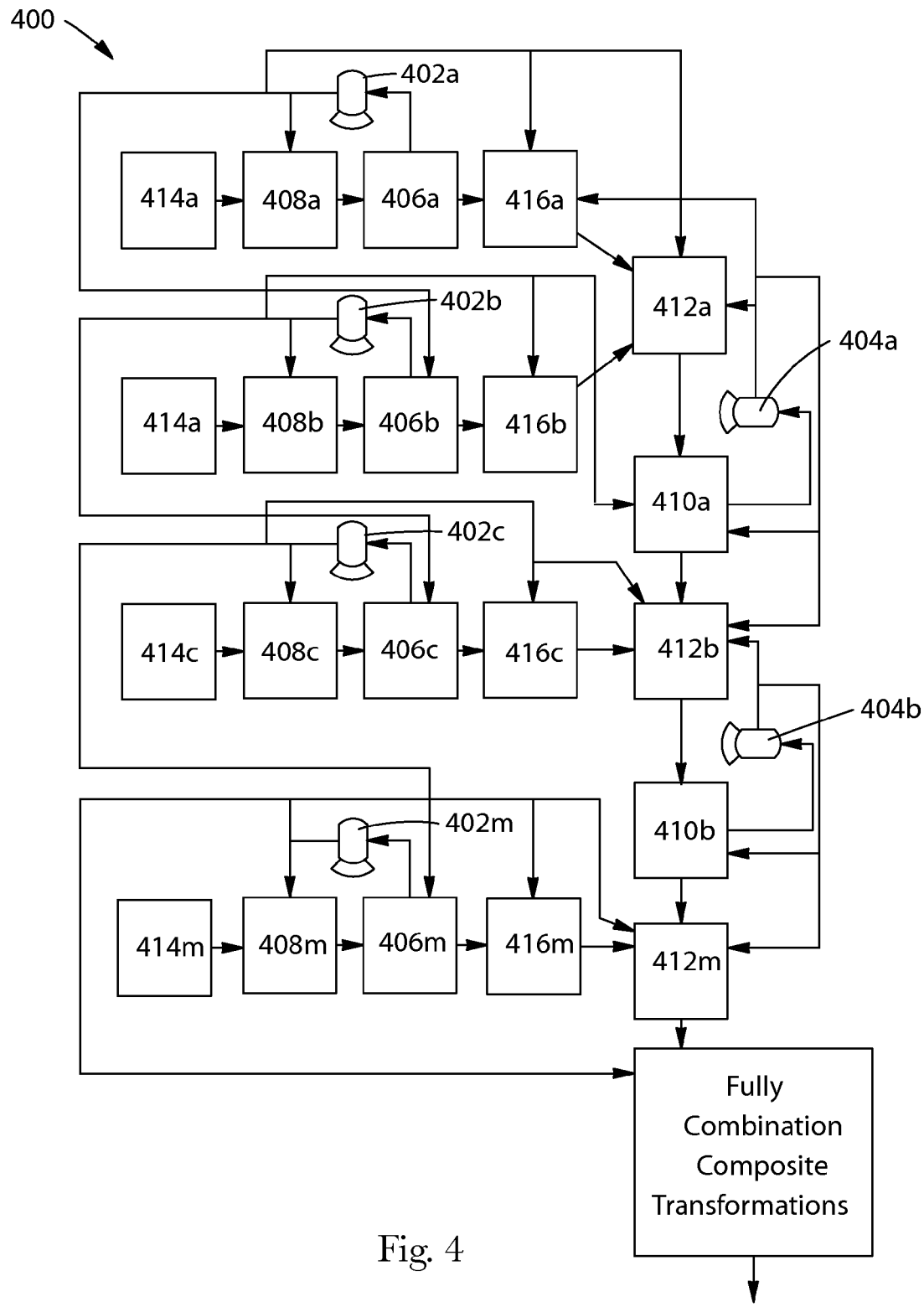
FIG. 4 is a schematic illustration of a manufacturing system.

Referring now to FIG. 4, a schematic illustration of a manufacturing system 400 is shown. Manufacturing system 400 may be scaled to accommodate any number of manufacturing processes to manufacture any number of different types of goods. As shown the subscripts "a," "b," "c," and "m" are intended to denote a numerical range of values from the number one to the variable "m." Where a plurality of similarly-labelled devices are shown (e.g., material delivery devices 414a, 414b, 414c, 414m), this is intended to be non-limiting and to convey that manufacturing system 400 may include any number of such devices (e.g., manufacturing system 400 may have one, two, three, etc., component delivery devices).

Manufacturing system 400 may include one or more material delivery devices (e.g., material delivery devices 414a, 414b, 414c, 414m) that provide component materials to manufacturing system 400 for further processing. A material delivery device may provide a raw material, semi-finished component, or a finished component, depending on its configuration. Non-limiting examples of material delivery devices include rollers, pumps, conveyor belts, and the like.

As shown, each component material is fashioned by manufacturing system 400 into individual components by any number of transformation devices. For example, a component material provided by material delivery device 414a may be transformed by a first transformation device 408a, an intermediary transformation device 406a, and/or a final transformation device 416a. As can be appreciated, any number of component transformation devices may be used in manufacturing system 400 to process an individual component. For example, a first component may be processed by a single transformation device 408a (e.g., intermediary transformation device 406a and final transformation device 416a may be omitted), by two transformation devices 408a, 406a (e.g., final transformation device 416a may be omitted), by three transformation devices 408a, 406a, 416a, or by more than three transformation devices (e.g., additional transformation devices may perform transformations between the transformations performed by the first transformation device 408a and intermediary transformation device 406a and/or between intermediary transformation device 406a and final transformation device 416a).

In addition to performing component transformations on individual components, manufacturing system 400 may also include any number of transformation devices that combine components (e.g., a first combining device 412a, a second combining device 412b, an $m^{th}$ combining device 412m, and the like). Manufacturing system 400 may also include any number of transformation devices that perform transformations on combined components (e.g., a first transformation device 410a, a second transformation device 410b, and the like). As can be appreciated, manufacturing system 400 may be scaled to accommodate any number of different combinations of components by adding or removing transformation devices, as needed.

As shown, manufacturing system 400 may also include any number of vision systems that monitor the processing of individual components (e.g., vision system 402a, 402b, 402c, 402m) and/or the processing of combined components (e.g., vision systems 404a, 404b). In some cases, a transformation device may trigger a vision system to capture images of components as the components pass the vision system. For example, an intermediary transformation device 406a performing a component transformation may trigger vision system 402a to capture an image. The one or more vision systems in manufacturing system 400 analyze images using virtual frames of reference to determine if other transformation devices in system 400 need to be adjusted (e.g., phased). For example, vision system 402a may determine that an upstream transformation device (e.g., first transformation device 408a, or the like) and/or downstream transformation device (e.g., combining device 410a, or the like) needs to be adjusted.

In a more detailed example of how manufacturing system 400 may be used to manufacture goods, reference will now be made with respect to manufacturing disposable absorbent articles. It is to be understood that this is intended to be a non-limiting example and that manufacturing system 400 may manufacture any number of different types of goods. A first material deliver device 414a may provide the core material to manufacturing system 400. The core material may comprise any number of different absorbent materials configured to absorb liquids. Similarly, a second material delivery device 414b may provide a back sheet and a third material delivery device 414c may provide a top sheet to manufacturing system 400. In general, a disposable absorbent article may be constructed by positioning an absorbent core material between an absorbent top sheet and a non-absorbent back sheet (e.g., by combining device 412b), crimping the sheets together (e.g., by transformation device 410b), and cutting the crimped sheets (e.g., by transformation device 412m).

Each individual material used to manufacture the disposable absorbent article may undergo one or more component transformations before being combined. For example, features, such as apertures, may be cut into the core sheet (e.g., by first transformation device 408a), individual cores may be cut from the core sheet (e.g., by intermediary transformation device 406a), and individual cores may be reoriented for further processing (e.g., by final transformation device 416a). Similarly, the top sheet, back sheet, and/or any other components used to manufacture the disposable absorbent article may undergo any number of transformations prior to being combined.

Figure 5A:
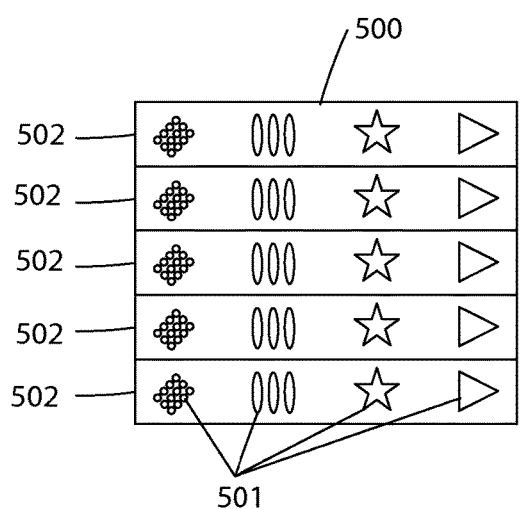
FIG. 5A is an illustration of a core sheet having uniformly-oriented features.
Figure 5B:
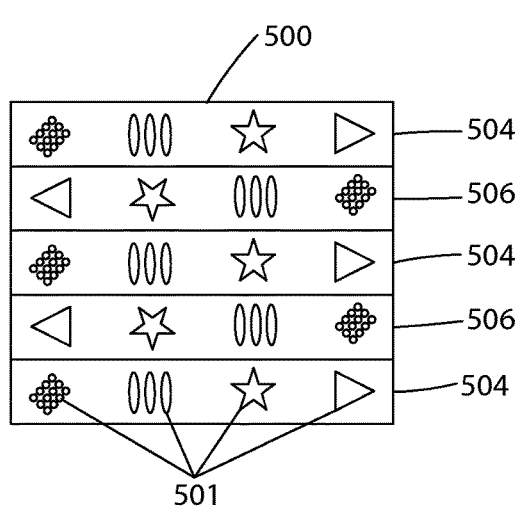
FIG. 5B is an illustration of a core sheet having features with alternating orientations.

Referring now to FIGS. 5A and 5B, illustrations of a core sheet 500 are shown as non-limiting examples. As shown, features 501 are placed onto core sheet 500 by one or more transformations and core sheet 500 is cut into individual cores 502 by further transformations. For example, features 501 may be apertures that are cut into core sheet 500 in order to increase absorbency. In another example, features 501 may be designs applied to core sheet 500.

Any number of orientations of individual cores may be produced from core sheet 500. For example, as shown in FIG. 5A, features 501 are oriented in a uniform direction and core sheet 500 may be cut to produce individual cores 502 having a uniform orientation. However, as shown in FIG. 5B, features 501 are applied to core sheet 500 in alternating positions, thereby creating two different populations of individual cores (e.g., cores 504 and 506). In further examples (not shown), any number of different populations of individual cores may be produced using core sheet 500.

In other transformations, individual cores may be cut from a core sheet and the cores reoriented for further processing. For example, if two populations of cores are created by applying features in alternating directions, the resulting individual cores may later be reoriented into a single orientation in the machine direction. As can be appreciated, individual cores may be reoriented into any number of different directions, thereby creating any number of different populations of individual cores.

Figure 6A:
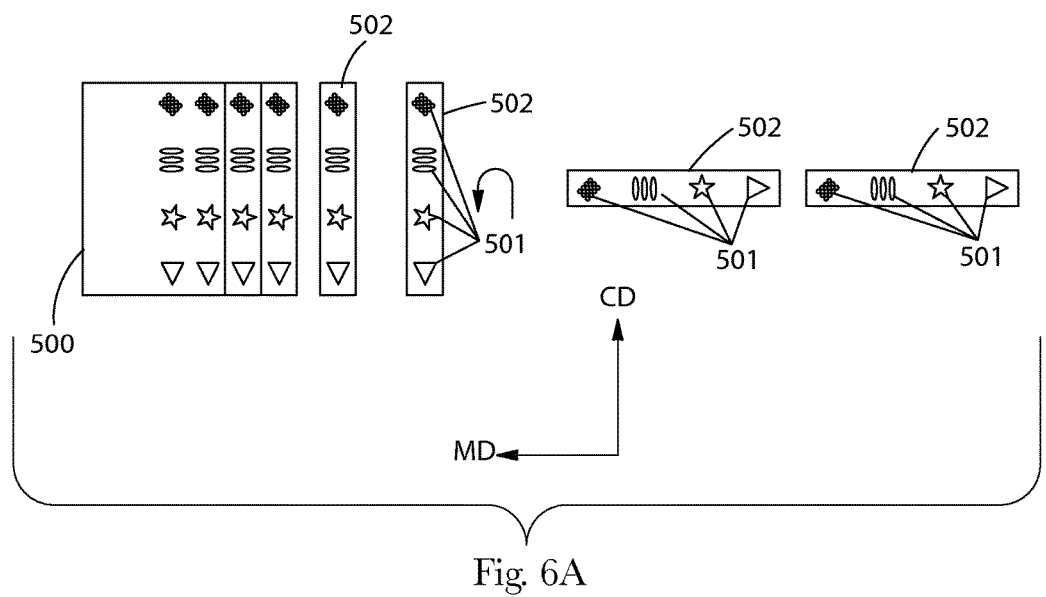
FIG. 6A is an illustration of uniformly-oriented cores being turned to have a uniform orientation in the machine direction.
Figure 6B:
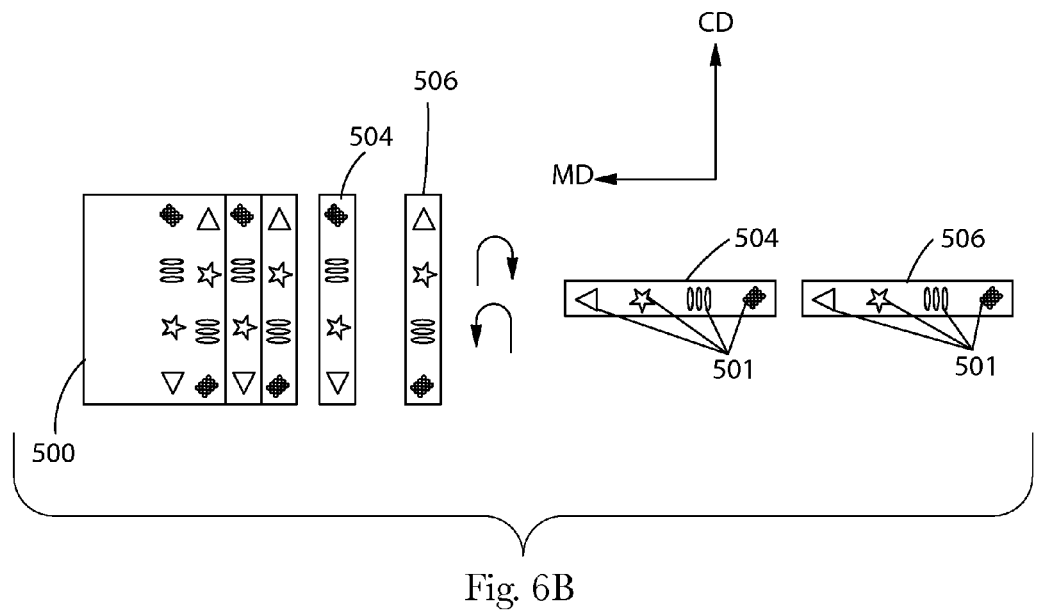
FIG. 6B is an illustration of cores having alternating orientations being turned to have a uniform orientation in the machine direction.
Figure 6C:
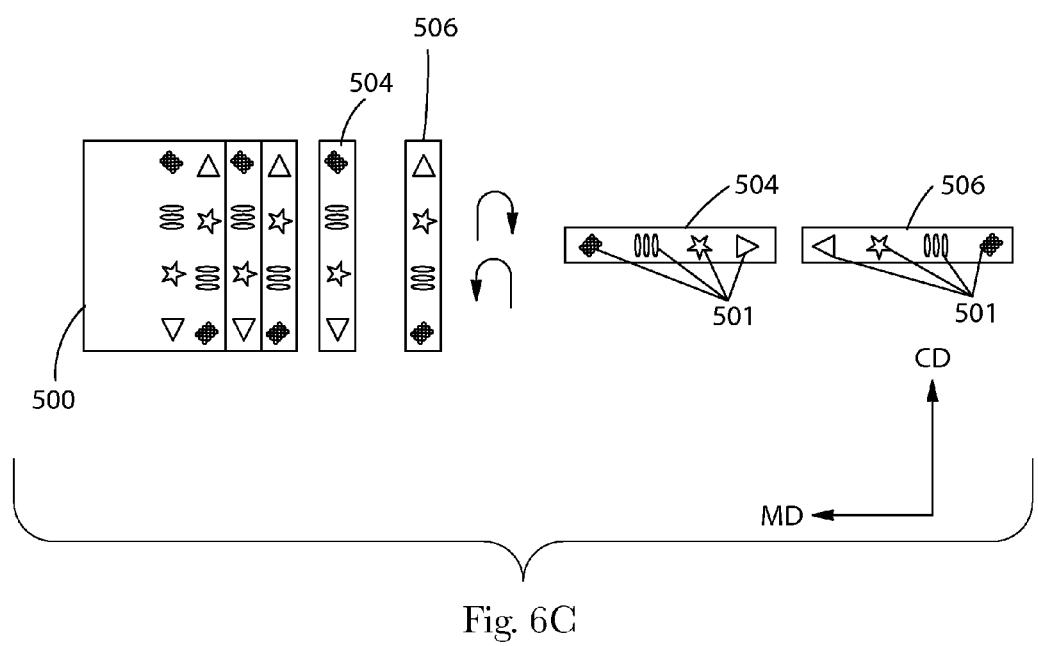
FIG. 6C is an illustration of cores having alternating orientations being turned to have alternating orientations in the machine direction.

Referring now to FIGS. 6A-6C, illustrations of transformations of core sheet 500 are shown as non-limiting examples. In FIG. 6A, features 501 are placed onto core sheet 500 in a uniform direction. Individual cores 502 are later cut from core sheet 500 and turned for further processing by the manufacturing system, such that individual cores 502 have a uniform orientation. In FIG. 6B, features 501 are placed onto core sheet 500 in alternating directions, creating two populations of cores 504 and 506. Again, individual cores 504, 506 are cut from core sheet 500 and then turned to have the same orientation in the machine direction. In FIG. 6C, features 501 are placed onto core sheet 500 in alternating directions, cut into individual cores 504, 506, and then reoriented such that individual cores 504 and 506 have alternating orientations after being turned. As can be appreciated, any number of different transformations involving applying features to a core sheet, cutting the core sheet into individual cores, and reorienting the cores may be used.

Referring again to FIG. 4, one example of how system 400 may be used to manufacture a disposable absorbent article can be seen, based on the foregoing. A sheet of core material may be unwound by material delivery device 414a and features may be added to it by a first transformation device 408a. An intermediary transformation device 406a cuts the core sheet into individual cores, and a final transformation device 416*a* then reorients the cut cores for further processing in system 400. Vision system 402*a* may be triggered by the processing of intermediary transformation device 406*a*, thereby causing an image of the core sheet to be captured. A controller of the vision system 402*a* then analyzes the image to ensure that the locations of the component in the image and/or the features on the component are properly placed within the image. For example, a possible setpoint used by the controller as part of this determination may correspond to a virtual cut line (e.g., where the intermediary transformation device 406*a* is expected to cut the core sheet into an individual core). If the locations of the component and/or features are not located at a setpoint or within a predefined setpoint range (e.g., the difference between a measurement and a setpoint is above a threshold value), the controller of vision system 402*a* may provide a phasing command (e.g., an adjustment command) to first transformation device 408*a*. In some cases, the controller may additionally provide an alert to a user or other computing device.

Further component transformations used to manufacture a disposable absorbent article may include placing individual cores between a top sheet and a back sheet, crimping the top sheet and back sheet, and cutting the sheets. For example, as shown in FIG. 7A (a section view), a core 502 may be combined with a top sheet 700 and back sheet 702, such that core 502 is positioned between them. Top sheet 700 and core 502 are configured to absorb liquid, while back sheet 702 acts to retain excess liquid that may pass through core 502. In FIG. 7B, a topview of the combined components is shown. The orientation of core 502 within top sheet 700 and back sheet 702 depends on how core 502 is oriented by a core turning transformation is performed by a component transformation device (e.g., final transformation device 416*a*).

Referring back to FIG. 4, combining devices 412*a* and 412*b* may operate to position an individual core between a top sheet and a back sheet. A transformation device 410*b* then crimps the top sheet and back sheet in order to secure the individual core between them. Vision system 404*a* and/or 404*b* may observe the combined components and adjust one or more transformation devices in manufacturing system 400 accordingly. In some cases, the capturing of an electronic image by vision system 404*a* and/or 404*b* may be triggered by the performance of a transformation by a transformation device. For example, transformation device 410*b* may provide a trigger to a vision system 404*b*, indicative of when a top sheet and back sheet are crimped.

Vision system 404*b* may analyze the characteristics of any number of subpopulations of components. In some cases, a subpopulation may include every nth component that passes vision system 404*b*, where n is greater than one. For example, a subpopulation may include every other component, every third component, every fourth component, etc. Vision system 404*b* may also analyze each subpopulation individually and/or compare different subpopulations, in order to determine if a phasing command is needed. For example, if a turner orients components into three different orientations, vision system 404*b* may analyze three different subpopulations of components using virtual frames of reference, where each subpopulation corresponds to a different orientation from the turner. In some cases, vision system 404*b* may also determine one or more mathematical characteristics of a subpopulation. A mathematical characteristic of a subpopulation may be any characteristic that generalizes position values for components within the subpopulation. In non-limiting examples, a mathematical characteristic may be an average CD position, an average MD position, an aggregate CD position, or an aggregate MD position. In other cases, vision system 404*b* may determine a mathematical characteristic across multiple subpopulations, in order to determine if a phasing command is needed. In a non-limiting example, vision system 404*b* may compare the average MD position of the previous fifty components to a threshold, in order to determine if a phasing command is needed.

If components are turned in two or more different orientations (e.g., subpopulations), the turning component transformation may have an effect on both the CD position and the MD position of the components. For example, since the position of an individual core component crimped between sheet components affects the overall quality of the disposable absorbent article, vision system 404*b* may adjust the phasing of a turner that turns the individual core component (e.g., final transformation device 416*a*). In cases in which the turner creates two or more differently oriented sets of core components, the vision system 404*b* may maintain running averages of the CD placements for each of the two subpopulations. The vision system 404*b* may then analyze the difference between the average CD placements of the two subpopulations, to determine if phasing is necessary. If the difference exceeds a predefined threshold, a phasing command may be sent to the turner. In another case, the average CD placement of an individual subpopulation may be compared to a threshold value, to determine if a phasing command is needed. Analysis of CD placements may be repeated to verify that the phasing command caused the CD placements to move below the threshold. If the difference between the CD placement and the threshold increased, a phasing command may be provided by vision system 404*b* to the turner corresponding to the opposite direction. In addition, if the difference is greater than a second threshold (e.g., larger than the first threshold), vision system 404 may disable the issuance of phasing commands altogether and issue an alert to an operator and/or another computing device.

Vision system 404*b* may also maintain a running average of MD placement values for a set number of components (e.g., across multiple subpopulations). The controller may generate a target setpoint for this average versus the assumed position of the leading edge of the MD cut to be performed by a transformation device 412*m* (e.g., a cutter that cuts the crimped sheets). If the average MD placement moves outside of the range defined by the setpoint plus or minus a predefined range, the controller provides a phasing command to a transformation device 410*b* and/or transformation device 412*m* (e.g., a crimper and/or cutter). For example, if the average MD placement is outside of the acceptable range, this may indicate that components are arriving at one or more downstream transformation devices earlier or later than expected. In this case, the controller may send a phasing command to an upstream and/or downstream transformation device to advance or retard a transformation device, in order to correct the timing of the manufacturing system.

Although the systems and methods disclosed are primarily described in relation to a manufacturing system for disposable absorbent articles, it is to be understood that this is illustrative only and not intended to be limiting. It is contemplated that the teaching of the present disclosure may be applied to any type of manufacturing system, without deviating from the scope of the present disclosure. For example, a virtual frame of reference may be based on a cutting operation that has not yet been performed in a manufacturing system for disposable absorbent articles or may be based on the future placement of a racing stripe in a manufacturing system for an automobile. Similarly, the vision system described herein can be adapted to provide phasing control over any type of machinery in a manufacturing process and is not intended to be limited to those machines used to manufacture disposable absorbent articles.

Many modifications and variations are possible in light of the above description. The above-described descriptions of the various systems and methods may be used alone or in any combination thereof without departing from the scope of the invention. Although the description and figures may show a specific ordering of steps, it is to be understood that different orderings of the steps are also contemplated in the present disclosure. Likewise, one or more steps may be performed concurrently or partially concurrently. It is therefore intended to cover in the appended claims all such changes and modifications that are within the scope of this disclosure.

What is claimed is:

1. A computerized method for controlling component transformations in a manufacturing system, the computerized method comprising the steps of:
    periodically capturing a first electronic image of a web of absorbent core material prior to a cutting device which cuts the web of absorbent core material into discrete absorbent cores and providing the first electronic image to a controller;
    utilizing a virtual cut line as a setpoint for the first electronic image of the web of absorbent core material;
    comparing a location value of the web of absorbent core material to the setpoint;
    generating a first phasing command for the cutting device based on the comparison between the location value and the setpoint;
    combining the discrete absorbent cores with a web of backsheet material at a first transformation device;
    periodically capturing a second electronic image of the discrete absorbent cores on the backsheet material and providing the second electronic image to the controller;
    comparing the second electronic image of the web of backsheet material and discrete absorbent cores with a first machine direction setpoint and a first cross direction setpoint and generating a second phasing command as needed for the first transformation device;
    combining the discrete absorbent cores and web of backsheet material with a web of topsheet material at a second transformation device;
    periodically capturing a third electronic image of the combined web of topsheet material, discrete absorbent cores and web of backsheet material and providing the electronic image to the controller; and
    comparing the captured third electronic image of the web of topsheet material, discrete absorbent cores, and backsheet material to a second machine direction setpoint and a second cross direction setpoint and generating a third phasing command as needed for the second transformation device.

2. The method of claim 1 further comprising the step of placing features onto the absorbent core material.

3. The method of claim 2, wherein the features comprise a plurality of apertures.

4. The method of claim 2, wherein the features comprise designs applied to the absorbent core material.

5. The method of claim 1, further comprising the step of placing first features and second features onto the absorbent core material in an alternating fashion.

6. The method of claim 1, wherein the discrete absorbent cores are re-oriented from their cut position for further processing.

7. The method of claim 1, wherein the discrete absorbent cores comprise a first population of discrete absorbent cores and a second population of discrete absorbent cores, wherein at least one of the first population of discrete absorbent cores and the second population of discrete absorbent cores are turned to have the same orientation with one another for further processing.

8. The method of claim 1, wherein the discrete absorbent cores comprise a first population of discrete absorbent cores and a second population of discrete absorbent cores, wherein at least one of the first population of discrete absorbent cores and the second population of discrete absorbent cores are turned to have an alternating orientation with one another for further processing.

* * * * *